US00PP25129P3

(12) United States Plant Patent
Chaparro et al.

(10) Patent No.: US PP25,129 P3
(45) Date of Patent: Dec. 2, 2014

(54) PEACH TREE NAMED 'UFBEST'

(50) Latin Name: ***Prunus persica* (L.) Batsch**
Varietal Denomination: UFBest

(75) Inventors: Jose X. Chaparro, Gainesville, FL (US); Wayne B. Shermain, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 13/506,363

(22) Filed: Apr. 13, 2012

(65) Prior Publication Data

US 2013/0276179 P1 Oct. 17, 2013

(51) Int. Cl.
*A01H 5/00* (2006.01)

(52) U.S. Cl.
USPC ..... Plt./197

(58) Field of Classification Search
USPC ..... Plt./197
See application file for complete search history.

(56) References Cited

U.S. PATENT DOCUMENTS

PP14,764 P2 5/2004 Sherman
PP20,294 P2 9/2009 Chaparro

*Primary Examiner* — Kent L Bell
(74) *Attorney, Agent, or Firm* — Dentons US LLP

(57) ABSTRACT

'UFBest' is a new and distinct variety of peach tree which has a winter chilling requirement slightly less than 100 chill units. The tree is of large size and is highly vigorous with a semi-spreading growth habit. Flowers are showy and pink and leaf glands are small and reniform in shape. Trees are self fertile and regularly bear heavy annual crops of early season fruit which are large for its ripening season. Fruit are firm, yellow, and non-melting, clingstone flesh. Fruit are uniform, substantially symmetrical shape, attractive, and have a bright red skin over nearly 100% of the deep yellow ground color. The fruit usually ripens 5 days before 'UFSun' in late April to early May at Gainesville, Fla.

1 Drawing Sheet

Latin name of the genus and species of the plant claimed: *Prunus persica* (L.) Batsch.

Variety denomination: 'UFBest'.

BACKGROUND OF THE INVENTION

The present invention relates to a new and distinct variety of peach (*Prunus persica* (L.) Batsch) tree which is named 'UFBest' and, more particularly to a peach tree which produces a high percentage of red skin with an attractive deep yellow ground color on the fruit. The fruit is of good eating quality with clingstone, non-melting, and yellow flesh. Fruit are mature for fresh market in late April to early May in Gainesville, Fla. Fruit are produced on a tree adapted to a mild winter climate. Contrast is made to 'UFSun' peach (U.S. Plant Pat. No. 14,764) for reliable description. This new variety 'UFBest' is a promising candidate for commercial success in that it retains fruit firmness from its non-melting flesh at the full flavor, tree ripe stage for a week on the tree.

This peach tree (genotype) originated in a cultivated area of the fruit breeding program located in Gainesville, Fla. The seed parent was 'FlordaBest' (U.S. Plant Pat. No. 20,294). The pollen parent was 'UFSun' peach. 'UFBest' was determined to have unique tree and fruit characteristics making it worthy for commercial fresh fruit production. When compared to 'FlordaBest', 'UFBest' produces fruit with non-melting flesh, while 'FlordaBest' is a melting flesh cultivar. In addition, 'UFBest' has a very low chilling requirement (~150 chill hours), allowing it to be planted and cropped in low chill (subtropical) locations such as south central Florida, while 'FlordaBest' has a higher chilling requirement (250+ chill hours), allowing it to be planted and cropped in north central Florida. In Gainesville, Fla., 'UFBest' ripens 10 to 30 days before 'FlordaBest' depending on the weather. 'UFBest' differs from 'UFSun' parent by having fruit with a higher percentage of red skin and by ripening one week earlier. 'UFBest' has a larger fruit size and more red in the skin than 'UFSun'. 'UFBest' peach tree was selected in 2007, and was designated and tested as Fla. 07-05C. It was asexually reproduced by budding on 'Flordaguard' (unpatented) seedling rootstock in Gainesville, where the selection was made and trees were also tested. Asexually propagated plants remained true to type. There are no known effects of this rootstock on this scion cultivar.

SUMMARY OF THE INVENTION

The new and distinct variety of peach tree bears yellow, non-melting flesh fruit with a high percentage of red skin. 'UFBest' peach tree blooms about 3 to 5 days before 'UFSun' peach at Gainesville, thus the estimated endodormancy requirement is less than the 100 chill units estimated for 'UFSun'. The present invention resulting in 'UFBest' peach tree is characterized by fruit of excellent flavor and eating quality. The trees are vigorous, productive, and without alternate bearing. Trees attain in two years, a height of 2.5 meters and a spread of two meters in Gainesville. Terminal growth of up to a meter annually is common on mature 4-year-old trees with normal pruning to a vase shape. The first fruit ripen in late April to early May in Gainesville or in about 80 days from full bloom. The fruit are uniformly large for an early season peach. The skin on ripe fruit has near 100% red over a yellow ground color. The flower anthers are light yellow, and petals are pink and showy. Leaf glands are small reniform.

BRIEF DESCRIPTION OF THE DRAWINGS

The accompanying drawing is a color photograph which shows a typical specimen of the fruit, leaf, and stem of the new variety as nearly true as it is reasonably possible to make in a color illustration of this type.

FIG. 1. Shows an attractive shape and exterior coloration of six specimens of fruit above a ruler in a stem end view, a blossom end view, side views facing and perpendicular to the suture, and fruit cut longitudinally showing the flesh with and without a pit.

DETAILED BOTANICAL DESCRIPTION

The tree, flowers, and fruit may vary in slight detail due to variations in soil type, cultural practices, and climatic condition. The potential for commercial production of fresh fruit by 'UFBest' peach tree is high, due to its attractive red skin over a bright yellow ground color, with good flavor balance of sugar and acid, and exceptional firmness due to its non-melting flesh. The present botanical description is that of the variety as grown for 4 years on 'Flordaguard' rootstock under the ecological conditions prevailing in Gainesville, Fla. Variations of the usual magnitude to changes in climatic growing conditions, soils, fertilization, pruning, irrigation, and pest control are to be expected. Colors (except those in common terms) are described from The Pantone Book of Color published by H. N. Abrams, Inc., N.Y. 1990.

Phenotypic Description of *Prunus persica* (L.) Batsch ('UFBest')

Tree:

*Size*.—Trees are large when trained to an open vase form.

*Vigor*.—Vigorous, and must be pruned in summer and winter to keep tree height restricted and to keep center of vase open. Trees respond typically to irrigation and fertilization. Tree growth of 5 to 7 feet in height and 4 to 6 feet in width occurs the first growing season in the field. Annual growth on mature trees averages 3 to 5 feet in length.

*Density*.—Light to Medium in branching habit (not overly twiggy), requiring pruning to open the tree center to permit high sunlight entrance for enhancing fruit color and sugar.

*Form*.—Semi-spreading.

*Hardiness*.—Hardy with respect to typical north central Florida winters. Chill units for endodormancy are estimated slightly below 100 chill units.

*Bearer*.—Annual and without alternate bearing, and fruit must be thinned to avoid limb breakage and to obtain large fruit size. Trees annually set several times the number of fruit for a desired crop load.

Trunk:

*Size*.—Large trunk diameter attaining 18 cm diameter at a height of 30 cm above the ground at the end of 4 years growth.

*Bark texture*.—Medium smooth, but changes to medium shaggy as tree ages.

*Bark color*.—Variable with older bark considered mostly gray, Flint Gray (Pantone 16-5803).

*Lenticels*.—Moderate number (18 per 4 square inches of surface area of trunk) and small (2-8 mm length) with the center closed.

*Lenticel color*.—Adobe (Pantone 17-1340).

Branches:

*Size*.—Strong growth of scaffold branches. This is not distinctive of the variety.

*Texture*.—Relatively smooth, medium amount of lenticels (18 lenticels per 4 square inches of trunk surface) attaining size found on trunk and old scaffolds. Roughness increases with age.

*Color*.—New wood is light green, Sweet Pea (Pantone 15-0531); Old wood is more brown, Pecan Brown (Pantone 17-1430).

*Crotch angles*.—Angles selected at 45 to 80 degrees in first year of tree training. Natural angles are within the normal range of standard varieties for a semi-spreading tree.

Leaves:

*Size*.—Medium; 14 to 16 cm length, including the petiole; 3.6 to 3.9 cm width in mid-shoot on vigorous upright summer growth.

*Thickness*.—Regular and average for peach varieties. Not distinctive of the variety.

*Form*.—Lanceolate with an acuminate tip, cuneate base, and serrulate leaf margins that are lightly undulate.

*Surface*.—Upper, glabrous; Lower, medium large veins that are pinnately netted.

*Color*.—Lower surface is green, Oasis (Pantone 16-0540); Upper surface is slightly darker green, Cactus (Pantone 18-0130).

*Glands*.—Two to four, small, reniform glands mostly on lower leaf blade, but occasionally on petiole. Leaf glands are light green, Chartreuse (Pantone 15-0751) on first full size leaves in mid-summer.

*Petiole*.—Average 11 mm length; 2.5 mm diameter. Color is light green, Sweet Pea (Pantone 15-031) on young full-sized leaves of summer.

*Stipules*.—Medium in length (5 to 8 mm), abscising just before the leaf obtains full size, both common to most peach varieties, and 2 per node.

*Arrangement*.—Alternate.

Flower buds:

*Abundance*.—Moderately high, most buds set fruit in absence of spring frosts.

*Size*.—Medium, average 2.5 mm length in late summer.

*Diameter*.—2.5 mm, diameter does not vary significantly between cultivars.

*Form*.—Plump, conic.

*Surface*.—Pubescent scales.

*Color*.—Brown, Copper Brown (Pantone 18-1336) in late summer.

Flowers:

*Hardiness*.—Hardy with respect to north central Florida winters. No flower bud damage observed during endodormancy at a low of 16° F.

*Blossom period*.—Three to 5 days before 'UFSun' peach — average January 19-25 at Gainesville, occurring over a 7 to 10 day period, dependant on ambient temperature.

*Aroma*.—Fragrance is slight to non-existent as is normal for most peach varieties.

*Type*.—Showy, location and seasonally variable in size, but within the range of commercial varieties. Average flower diameter — 35 mm. Average petal length, 18 mm; width, 14 mm. Petals are obovate and edges vary from smooth to slightly undulate.

*Color* (*upper and lower surfaces*).—Pink, Orchid Pink (Pantone 13-2010) at full size flower.

*Flower parts*.—Pistil shape and color are within the range of standard commercial varieties. There are 5 sepals and 5 petals. Sepals are pubescent and petals glabrous. Sepal shape, size, and color do not vary significantly between cultivars. Pistils are usually 1 per flower and pubescent. Pistil length (from tip of stigma to base of ovary) is 16 to 18 mm; Pistil color is light green, Pale Star (Pantone 12-0626). Flower pedicel is 5 to 8 mm length, not distinguishing for the variety.

*Anthers*.—Yellow, Golden Cream (Pantone 13-0939) at flower opening.

*Stamens*.—Number varies from 35 to 45. Length is 9 to 16 mm.

*Pollen*.—Abundant and light yellow, Lemon Drop (Pantone 12-0736).

*Calyx cup*.—Medium large (5 mm diameter at the top and 5 mm depth).

*Flower depth*.—5 mm, depth of calyx cup.

*Fertility*.—Self fertile, and no cross pollination is required.

Fruit:

*Maturity when described*.—Tree-ripe fruit on Apr. 27, 2011 in Gainesville.

*Date of first picking*.—Apr. 20, 2011 at Gainesville.

*Date of last picking*.—May 2, 2011 at Gainesville.

*Size*.—Uniform, medium large (large size for early season maturity at 100 to 120 g). Varies with number of fruit per tree, soil type, climate, and cultural practices.

*Average equatorial diameter*.—2½ inches (63 mm).

*Average polar length* (*stem to distal end*).—2⅜ inches (61 mm).

*Pedicel*.—Length — 7 to 9 mm; Width — 3 to 4 mm. Color is green, Golden Green (Pantone 15-0636).

*Longitudinal section form*.—Nearly round.

*Transverse section through diameter*.—Round.

*Suture*.—Inconspicuous in form and color.

*Ventral surface*.—Rounded.

*Base*.—Slightly retuse.

*Apex*.—Round to slightly obtuse.

*Crater at pedicel*.—Flaring circular. Stem depressing on base of fruit. Crater depth is 6 to 10 mm, breadth is 22 mm at top and 3 mm at pedicel attachment.

*Skin*.—Thickness — Medium, not a distinguishing feature. Texture — Medium short pubescence, similar to that of 'UFSun' peach. Tenacity — Tenacious to flesh. Color — Dark red, Pompeian Red (Pantone 18-1658) over 90 to 100% of the skin. Ground color is yellow, Banana (Pantone 13-0947). Fruit exposed to the sun have an enhanced red skin. Tendency to crack — None observed. Taste — No astringency observed. Pubescence — Short, medium soft to touch.

*Flesh*.—Ripens — Evenly within each fruit and throughout the tree. Texture — Firm, fine, juicy, non-melting when fully ripe. Fibers — Very fine, small, tender, and abundant throughout the flesh. Aroma — Moderate and in the middle range of commercial peach varieties. Eating quality — Good, sweet, slightly acid. Fruit averaged near 12 brix when described. Juice — Abundant. Color — Yellow, Snapdragon (Pantone 13-0840) with a small amount of red, Hot Coral (Pantone 17-1656) throughout the flesh on stressed trees, especially under dry, hot conditions. There is no red at the pit. Browning by oxidation — Slight on tree ripe fruit beginning to soften. Amygdalin — Undetected.

*Stone*.—Type — Clingstone, adhering to flesh even at softening. Size — Medium small; average length is 28 mm; average diameter at the equator from dorsal to ventral side is 20 mm; average thickness at the equator across (facing) the suture is 18 mm; average wall thickness at the equator perpendicular to the suture is 5 to 6 mm. Color — Light brown, Wheat (Pantone 13-1016) when freshly exposed. Form — Oval shape with an acuminate tip and acute base. Sides — Near equal. Surface — Irregularly furrowed toward the ventral edge, pitted from the center toward the base and apex. Ridges — Jagged toward the base. Tendency to split — None observed. Kernel — Oval shape, bitter (amygdalin is abundant) with obtuse tip, germinating best with embryo culture. Average width, 10 mm; average length 15 mm; Color is brown, Topaz (Pantone 16-1150) when first removed from fresh fruit endocarp.

*Use*.—Fresh; dessert.

*Resistance to disease*.—High resistance to bacterial spot incited by *Xanthomonas campestris* pv. *pruni*. Resistance to other fruit and tree diseases are within the range for commercial peach cultivars in Florida. No unusual resistance or susceptibility or insects and diseases noted.

*Keeping quality*.—Excellent after 2 weeks at 35 F and with minimal bruises or scarring appearing on skin.

*Shipping quality*.—Degree of firmness at harvest and firmness retained in refrigeration for 2 weeks at 7 C with no internal breakdown of flesh or appreciable loss of eating quality indicates fruit should be highly acceptable for shipping.

What is claimed is:

1. A new and distinct peach tree variety as illustrated and described herein, characterized by an estimated slightly less than 100 chill unit requirement, and bearing early season fruit having firm, yellow, and non-melting flesh of high eating quality, and an attractive, high percentage red skin color with fruit ripening in late April to early May, or about 5 days before 'UFSun' in Gainesville, Fla.

* * * * *

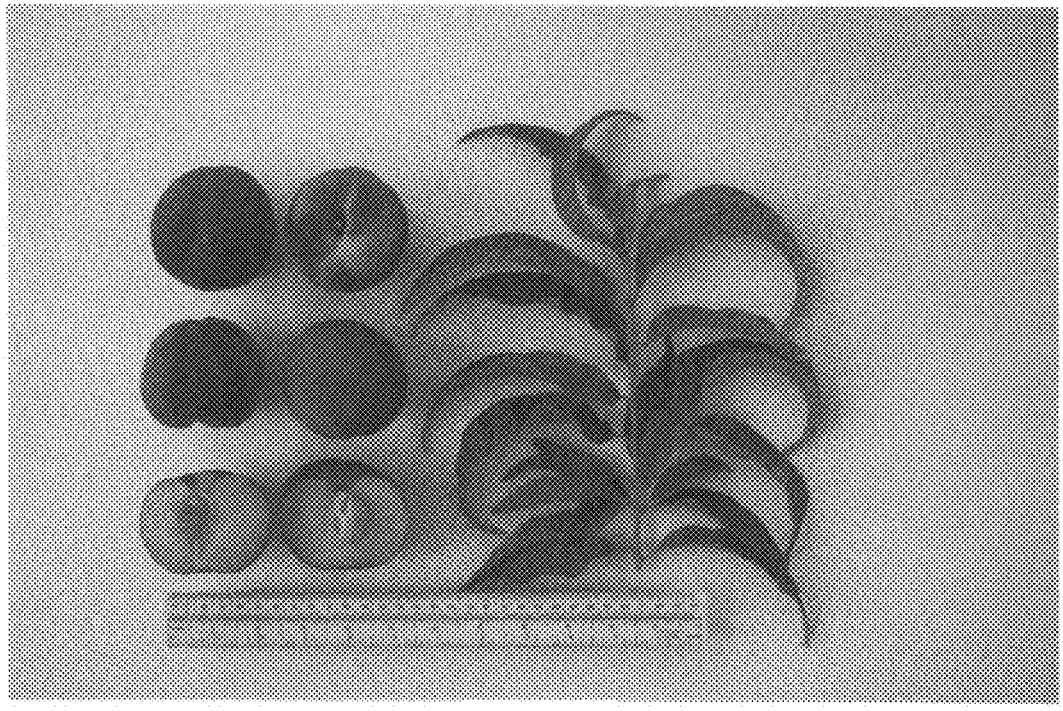

UNITED STATES PATENT AND TRADEMARK OFFICE

CERTIFICATE OF CORRECTION

PATENT NO. : PP25,129 P3
APPLICATION NO. : 13/506363
DATED : December 2, 2014
INVENTOR(S) : Jose X. Chaparro et al.

It is certified that error appears in the above-identified patent and that said Letters Patent is hereby corrected as shown below:

Title Page, Item (75), Please delete "Shermain" and insert --Sherman--

Signed and Sealed this
Twenty-first Day of July, 2015

Michelle K. Lee

Michelle K. Lee
*Director of the United States Patent and Trademark Office*